United States Patent [19]

Hoffman

[11] Patent Number: 4,475,236
[45] Date of Patent: Oct. 2, 1984

[54] METHOD FOR COUNTING OVERLAPPING CELL POPULATIONS IN A DISTRIBUTION HISTOGRAM

[75] Inventor: Robert A. Hoffman, Mansfield, Mass.

[73] Assignee: Ortho Diagnostic Systems Inc., Raritan, N.J.

[21] Appl. No.: 320,822

[22] Filed: Nov. 12, 1981

[51] Int. Cl.³ .............................................. G06K 9/00
[52] U.S. Cl. .......................................... 382/6; 377/10
[58] Field of Search ........................ 382/1, 6; 356/39; 364/416; 377/10, 11, 6

[56] References Cited

U.S. PATENT DOCUMENTS

| | | | |
|---|---|---|---|
| 4,071,891 | 1/1978 | Barrows | 377/10 |
| 4,284,355 | 8/1981 | Hansen et al. | 356/39 |
| 4,295,199 | 10/1981 | Curry et al. | 377/10 |
| 4,325,706 | 4/1982 | Gershman et al. | 356/39 |
| 4,330,745 | 5/1982 | Hayashi | 377/10 |
| 4,336,029 | 6/1982 | Natale | 436/172 |

Primary Examiner—John C. Martin
Assistant Examiner—Michael D. Parker
Attorney, Agent, or Firm—Mark A. Hofer

[57] ABSTRACT

A sample having a mixture of unknown stained cells and known cells having different staining characteristics is analyzed rapidly, a cell at a time, in a flow cytometry system having a sample stream dimension in the range of expected cell dimensions. The cells are illuminated with focused illumination and fluorescence is detected and related to the number of cells. The resulting histogram of the mixture sample may be analyzed by counting the cells in a controlled population below a relatively low threshold value of fluorescence intensity to form a first fraction and relating this fraction to the fraction of cells in the sample mixture below the threshold value of fluorescence intensity to determine the number of unknown cells in the sample mixture.

3 Claims, 5 Drawing Figures

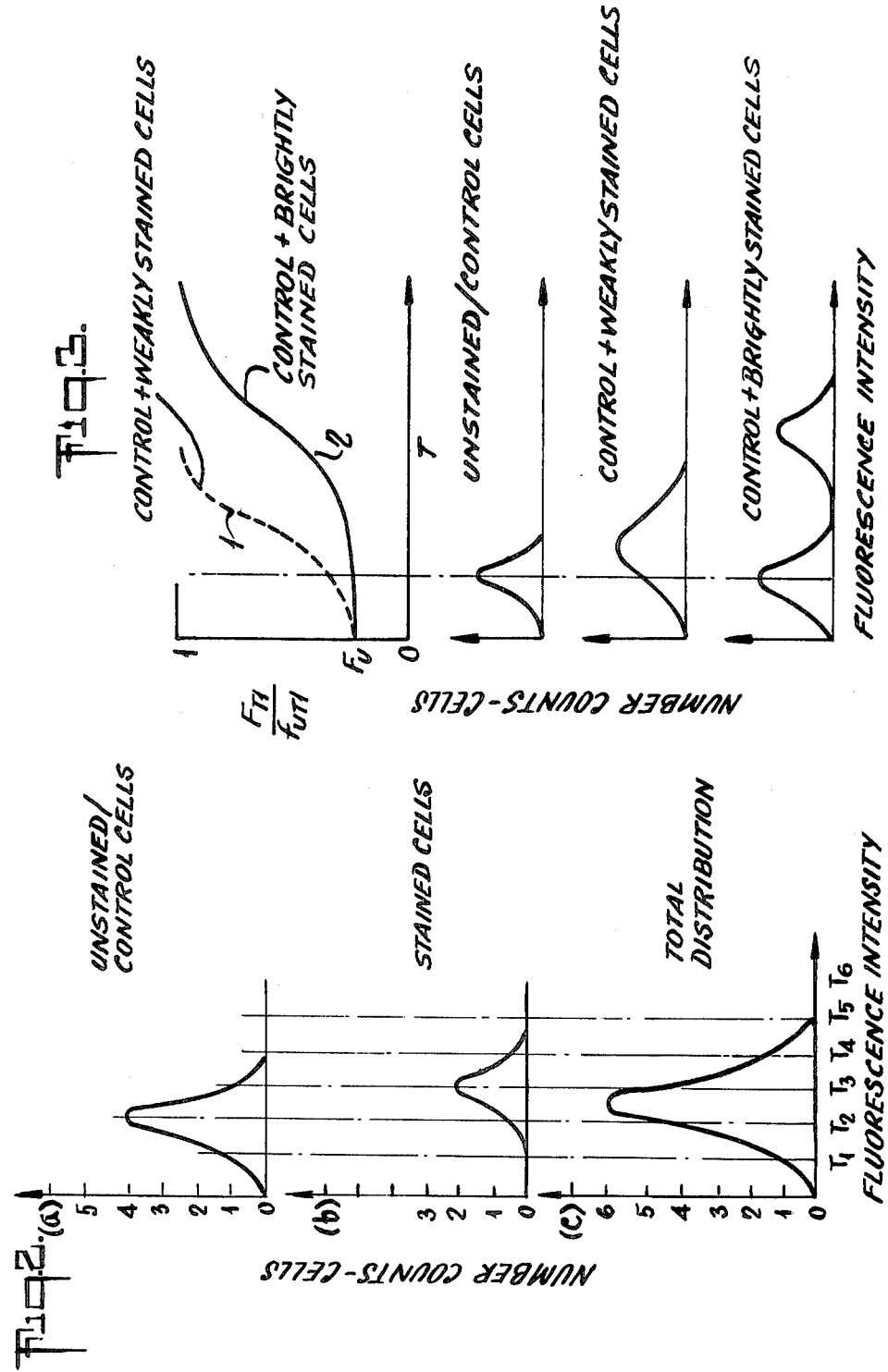

METHOD FOR COUNTING OVERLAPPING CELL POPULATIONS IN A DISTRIBUTION HISTOGRAM

FIELD OF THE INVENTION

This invention relates to the automatic analysis of blood or other cells, and more particularly to automated approaches for counting overlapping subpopulations of cells in a distribution histogram.

BACKGROUND OF THE INVENTION

Detection and enumeration of categories and types of blood cells comprising whole blood has provided extensive challenge to designers and manufacturers of automated hematology instruments. An approach to automated hematology which is increasingly finding acceptance as the preferred approach is one often designated as optical flow cytometry. Such systems employ a hydrodynamically focused stream in which blood cells are passed extremely rapidly, one at a time. The fluid stream is illuminated by precisely focused light, for example coherent radiation from a laser and the changes effected to such focused light by the passage of the cells is detected. Much can be determined by analysis of light scattered by the cells, and if the blood sample has been treated with specific staining agents, still more can be determined by a suitable analysis of fluorescent light stimulated from a stained cell or other fluorescent material passing through the focusing zone. Often the populations of cells passing through the focusing zone may be discriminated based on their relative ability to fluorescently stain or the inherent presence of fluorescing material within the cell thereby exhibiting distinct levels of fluorescence. Each such population by itself can be expected to exhibit a characteristic histogram relating fluorescent levels with the number of cells present. As is sometimes the case, however, mixtures of such populations will exhibit a histogram composed of overlapping subpopulation histograms. In these instances, it may be very difficult to separate the individual populations by means of histogram analysis.

One approach to this problem, taught in U.S. Pat. No. 4,325,706 to R. J. Gershman, et al entitled "Automated Detection of Platelets and Reticulocytes in Whole Blood, (commonly assigned)" involves making assumptions as to the distribution of the cells versus associated fluorescent light stimulations and thereaftrer fitting a Gaussian curve to the curve of the distribution at a point centering with its peak and then detecting deviations from said Gaussian curve by predetermined statistical functions.

It is an object of the present invention to provide yet another automated, effective and highly repeatable approach to the discrimination between subpopulations of cells whose individual histograms have been combined to form a common histogram.

SUMMARY OF THE INVENTION

In accordance with the principles of the present invention, there are provided methods for determining the number of unknown, stained cells in a sample having a mixture of both the unknown cells and a population of unstained cells. These methods involve providing the sample and a separate control population of known, unstained cells and passing them through an optical flow cytometry flow cell having a substantially narrowed hydrodynamic focal region. The cells are illuminated and the scattering and resulting fluorescence emitted are detected whereby the cells are counted. A relatively low threshold value of fluorescence intensity is selected and applied to the resulting histograms of both the cells of the sample and the cells in the controlled population. The number of control cells below the selected threshold value is counted as well as the total number of control cells and these two numbers are related to determine a first fraction. The cells in the sample that fall below the threshold value are counted as well as the total number of sample cells and these two numbers related to determine a second fraction. The first fraction and the second fraction are further related for discriminating the histogram of unknown, stained cells from the total number of cells in the sample mixture, and determining the fraction of unknown cells in the sample.

DESCRIPTION OF THE DRAWINGS

FIGS. 2a-2c diagrammatically represent histograms for control cell populations, unknown cell populations and mixed control and unknown populations respectively.

FIG. 3 demonstrates the principles of the invention as applied to populations that have limited or significant overlap of individual histogram representations.

BEST MODE FOR CARRYING OUT THE INVENTION

Figure 1:
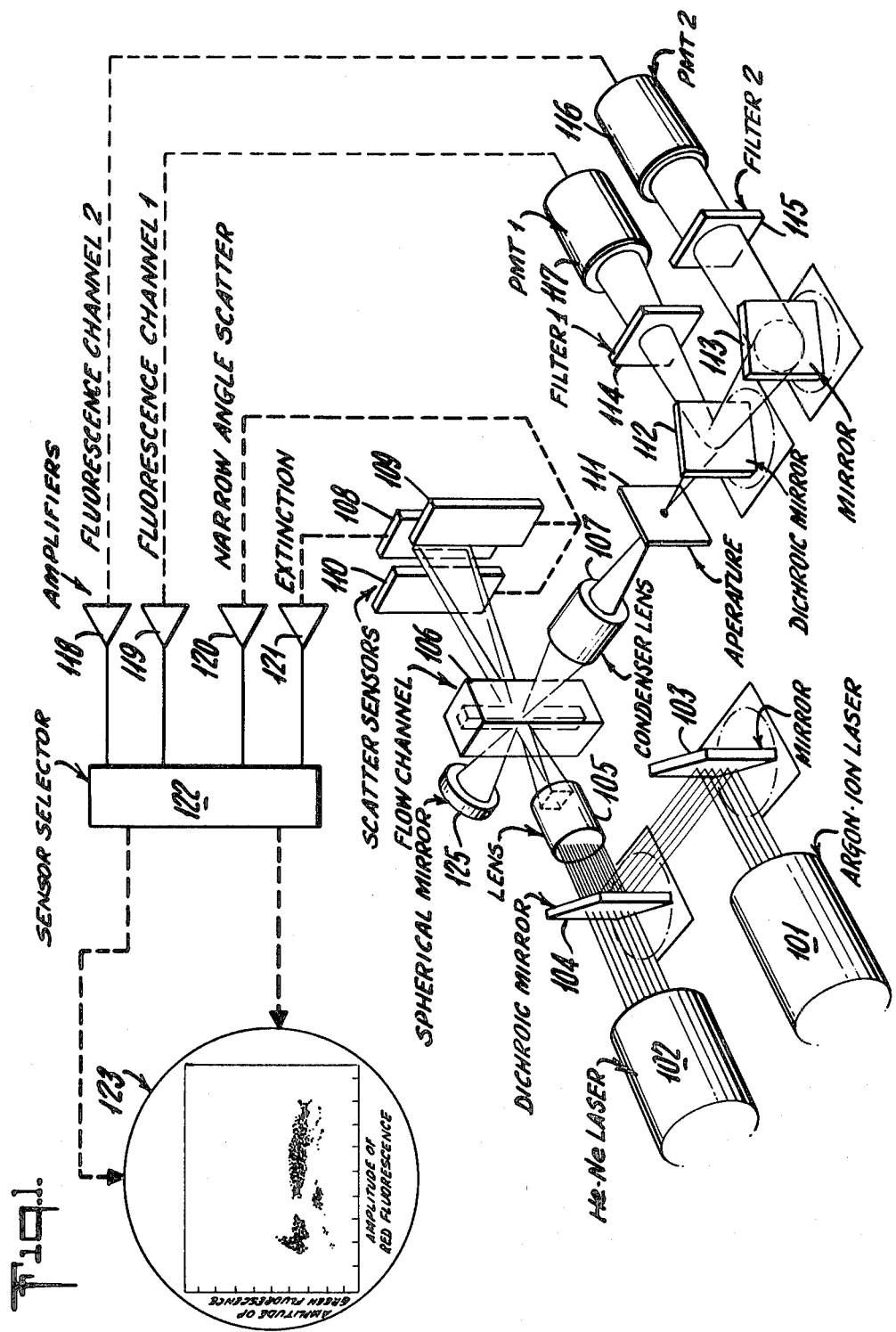
FIG. 1 shows a stylized version of a commercially available flow cytometric apparatus, which may be adapted for utilization in accordance with the principles of the present invention.

Referring first to FIG. 1, there is shown a stylized functional and structural representation of apparatus which may be utilized in accordance with the principles of the present invention. In fact, the apparatus of FIG. 1 depicts a particular system available commercially under the trade designation CYTOFLUOROGRAPH ™, which is sold by Ortho Diagnostic Systems Inc., Route 202, Raritan, N.J. 08869. The apparatus of FIG. 1 incorporates the principles of flow cytometry for cell analysis, and includes capacity for sensing fluorescent response of cells to specific types of illumination.

Focal to the FIG. 1 apparatus is a flow channel 106, wherein cells in liquid suspension are passed, in single file and at a rapid rate (e.g. 2,500 cells per second) through a sensing zone. The sensing zone is defined by the intersection of cell flow and an incident light beam, typically focused coherent light from a gas laser. As the cell passes through the sensing zone, it interacts with incident light in a variety of ways. Some light, of course, is absorbed by the cell, other light is scattered at relatively narrow angles to the axis of incident light, and still other light is scattered at angles quite divergent from the axis of incident light, for example at right angles to the incident light.

Furthermore, depending upon the nature of the cell itself, and any dyeing or staining to which the cell may have previously been subjected, fluorescence emissions may occur.

Accordingly, photosensors located at various orientations with respect to the cell stream and the incident laser light permit detection of a unique set of responses for each given type of cell. Thus FIG. 1 includes an argon ion laser 101 and a helium neon laser 102, with a coherent light emitted by each being variously deflected via mirrors 103 and 104 and a lens 105 to the sensing zone of the flow channel 106. As is known in the art, the cell sample stream is carried in laminar fashion within a flowing fluid sheath, to ensure that but a single cell will be illuminated in the sensing zone at a given time. Hence, as each cell is illuminated by light, interaction of the cell with a light may be sensed.

As shown in FIG. 1, an extinction sensor 108 detects the amount of light blocked by the cell, and forward light scatter is detected by photosensors 109 and 110 approximately in a cone of half angle 20°. Electrical signals generated by the sensors 108, 109 and 110 are coupled to amplifiers 120 and 121, which present electrical signals of suitable amplitude and the like for subsequent analysis and/or display.

In the apparatus of FIG. 1, light which is emitted from the cell by virtue of a fluorescence response is sensed at right angles both to the direction of cell flow and to the axis of incident light. A spherical mirror 125 and a condenser lens 107 collects this light approximately in a cone of half angle 20°, and couples this light through an aperture 111, successively to a dichroic mirror 112 and to a second mirror 113. A first color filter 114 (e.g. to pass relatively long wavelength light) conveys select light from the dichroic mirror 112 to photosensor 117 (e.g. a photomultiplier tube). A second filter 115 selectively passes light of a different color (e.g. relatively short wavelength light) from the second mirror 113 to a second photosensor 116. Electrical signals from sensors 116 and 117 in the form of pulses corresponding to light from respective cells, are coupled to amplifiers 118 and 119, thereby also to produce signals which are adapted for suitable processing.

As shown in the FIG. 1 embodiment, a sensor selector 122 generates output histograms utilizing signals from the amplifiers 118 through 121. For example, one usable form of output is a plot of amplitude of red fluorescence, from sensors 117, against amplitude of green fluorescence, from sensor 116. Such a histogram is shown at display 123, with each point on the histogram representing an individual cell. Clusters or aggregates of points on the histogram represent groups of cells of similar type. Quite evidently, those of ordinary skill in the art find it useful variously to generate histograms of narrow forward angles scatter versus intensity of green fluorescence, narrow forward angle scatter versus axial light extension, and so forth.

In accordance with the principles of the present invention, it is highly desirable to be able to automatically effectuate the discrimination between two closely overlapping subpopulations of cells which thereby produce one complex histogram which in turn is composed of the individual histograms of the subpopulations.

The most difficult problem in analyzing immunofluorescent histograms occurs when attempting to extract a population of positive or weakly fluorescent stained cells from a population of negative or unstained cells which may or may not exhibit their own inherent fluorescence. FIG. 2 diagrammatically illustrates the histograms involved. The histograms may be obtained by graphing fluorescence intensity against the number of counts or cells present. FIG. 2a illustrates the histogram of the control or unstained cell population having a total count of four at the peak and having the peak occur at an arbitrarily chosen threshold (T2) fluorescence intensity. FIG. 2b illustrates the shift of the peak to threshold 3 (T3) for weakly stained cells having a peak count of two. Upon combining the histograms represented in FIGS. 2a and 2b, the resulting histogram is illustrated in FIG. 2c having a peak count of six with a fluorescence intensity peak just to the right of threshold 2. Comparison of the histograms for the stained and unstained cells shows that upon chosing a value of fluorescence intensity at threshold 1, there is a population of unstained cells falling below this threshold whereas there are no stained cells falling below this level. In fact, the percentage of cells above and below the indicated thresholds for the different cell popultions can be represented as follows:

| Cell Type | % Cells Above Threshold | | | | % Cells Below Threshold | | | |
|---|---|---|---|---|---|---|---|---|
| | T1 | T2 | T3 | T4 | T1 | T2 | T3 | T4 |
| Unstained | 88 | 50 | 12 | 0 | 12 | 50 | 88 | 100 |
| Stained | 100 | 88 | 50 | 12 | 0 | 12 | 50 | 88 |
| Mixture 1:2 Stained to Unstained | 92 | 63 | 25 | 4 | 8 | 37 | 75 | 96 |

Since the mixture of stained and control cells was in the ratio of 1 to 2, the percentage of stained cells is 33 1/3 percent. A cursory glance through the tabulated values will show that none of the thresholds is useful for directly determining this percentage from the percent of positive cells. This is because at the higher values of fluorescent intensity there is a constant overlap between the stained and unstained cell populations. The percentages of each population, however, can be determined if the cells falling below threshold T1 are examined. In the mixed sample, it is observed that 8 percent of the cells fall below threshold T1 while in the control or unstained cell population, 12 percent of the cells have fluorescence falling below the threshold 1 value. By taking the ratio of the mixed sample percentage to the control sample percentage, we find that 66.7 percent of the total cells are unstained cells in the mixture. Since a simple proportion of 1 to 2 was chosen, it is evident that this percentage is indeed correct. The following mathematical analysis will show that the principles of the invention can indeed be applied to any mixture of populations to determine the unknown or stained portion of cells therein.

The following terms are defined:

T1-is the chosen threshold value of fluorescence intensity;

$I_{T1}$-the number of cells in the sample mixture below threshold T1;

$I_u$-the number of unstained cells;

$I_s$-the number of stained cells.

We know that the total number falling below threshold T1 is composed of the summation of the fractional amount of the number of the unstained cells falling below T1 with the fractional amount of the number of stained cells falling below T1 or $$I_{T1} = (I_u)(f_{uT1}) + (I_s)(f_{sT1}) \qquad 1.$$

where $f_{uT1}$=the fractional amount of unstained cells falling below threshold T1 and $f_{sT1}$ is the fractional amount of stained cells falling below threshold T1, and $f_{uT1}$ is determined by applying an unstained, control sample. At this point, two assumptions are made, (1) the fluorescence intensity mean of the stained population is greater than the fluorescence intensity mean of the unstained control and (2) the shape of the control distribution is unchanged in the sample-mixed population, i.e., the stain distribution is drawn randomly from the control unstained population.

We also know that the total number of cells equals the summation of the individual numbers of cells in the unstained and stained cell populations. In other words, $$I_{TOT} = I_u + I_s. \qquad 2.$$

Dividing both sides by $I_{TOT}$ we get:

$$\frac{I_{T1}}{I_{TOT}} = \frac{(I_u)(f_{uT1})}{I_{TOT}} + \frac{(I_s)(f_{sT1})}{I_{TOT}} \qquad 3.$$

We know that the fractional number or population of cells ($F_{subscript}$) is related directly to the number of cells, in other words:

$$F_{subscript} = I_{subscript} \div I_{TOT} \qquad 4.$$

Making the appropriate manipulations we arrive at:

$$F_{T1} = F_u(f_{uT1}) + F_s(f_{sT1}) \qquad 5.$$

We further know that the fractional population of unstained cells in summation with the fractional population of stained cells equals one, i.e.:

$$F_u + F_s = 1. \qquad 6.$$

Therefore:

$$F_{T1} = F_u(f_{uT1}) + (1 - F_u)(f_{sT1}) \qquad 7.$$

And subtracting $(f_{uT1})$ from both sides yields:

$$F_{T1} - (f_{uT1}) = F_u(f_{uT1}) - (F_{uT1}) + (1 - F_u)(f_{sT1}) \qquad 8.$$

And:

$$F_{T1} - (f_{uT1}) = (F_u - 1)(f_{uT1}) + (1 - F_u)(f_{sT1}) \qquad 9.$$

And:

$$F_{T1} - (f_{uT1}) = (-1)(1 - F_u)(f_{uT1}) + (1 - F_u)(f_{sT1}) \qquad 10.$$

And:

$$F_{T1} - (f_{uT1}) = (f_{sT1} - f_{uT1})(1 - F_u) \qquad 11.$$

And:

$$F_{T1} - (f_{uT1}) = (f_{sT1} - f_{uT1})(F_s) \qquad 12.$$

And:

$$\frac{(F_{T1}) - (f_{uT1})}{(f_{sT1}) - (f_{uT1})} = F_s \qquad 13.$$

Or:

$$F_s = \frac{\frac{F_{T1}}{f_{uT1}} - 1}{\frac{f_{sT1}}{f_{uT1}} - 1} \qquad 14.$$

Multiplying top and bottom by $(-1)$ yields:

$$F_s = \frac{1 - \frac{F_{T1}}{f_{uT1}}}{1 - \frac{f_{sT1}}{f_{uT1}}} \qquad (15.)$$

where $F_s$ is the fractional population of stained cells within the sample mixture and $F_{T1}$ and $f_{uT1}$ are both known quantities and are the fractional population of all cells of the sample falling below threshold T1 and the fraction of unstained population of cells falling below T1 respectively. The only unknown is $f_{sT1}$ which is the fraction of stained population falling below T1. Since equation 15 is in terms of an unknown, an exact solution is not mathematically possible, however, the relationship is extremely useful. In fact, in conjunction with assumption 1, only two cases of distinction arise.

CASE 1

If $f_{sT1}$ Is much less than $f_{uT1}$, i.e., the fractional stained component below threshold T1 is much less than the fractional unstained component falling below T1

$$\text{then: } \frac{f_{sT1}}{f_{uT1}} \longrightarrow 0$$

and $F_s$ may be approximated by:

$$F_s \approx 1 - \frac{F_{T1}}{f_{uT1}} \qquad 16.$$

Thus, the fractional composition of stained cells in a mixed population sample is now in terms of the fractional composition of the total number of cells in the sample falling below threshold T1 and the fraction of unstained or control cells falling below threshold T1, both quantities of which are measurable and thus known.

CASE 2

If the fractional stained component falling below threshold 1 is significant in comparison to be fractional unstained component falling below threshold 1, i.e., $f_{sT1}$ is less than $f_{uT1}$ then the following relationship holds true:

$$F_s \geq 1 - \frac{F_{T1}}{f_{uT1}} \qquad 17.$$

Even if the distributions of stained and unstained cell populations overlap significantly below threshold T1, one can still place a lower limit on the fraction of stained cells in the sample.

Practically one may, with great facility, determine whether Case 1 or Case 2 is properly applicable by plotting $F_{T1}/f_{uT1}$ as a function of threshold value T. When one is in a region of chosen threshold values where the stained population does not significantly overlap the unstained or control population then, $F_{T1}/f_{uT1}$ is nearly constant and equal to $F_u$ and Case 1 applies.

This is schematically illustrated in FIG. 2. When $F_{T1}/f_{uT1}$ is relatively constant as illustrated by curve 2 in FIG. 3, it can be seen that the curve is composed of two populations having clearly different fluorescence intensities and thus the control population is much less fluorescent than the brightly stained cell population as can be seen in the count or population curve (c). However, when the populations of cells are not so clearly distinguishable, i.e., the control cells are weakly stained and the unknown cell population has a fluorescence intensity only slightly greater, then it can be seen that the resulting plot of $F_{T1}/f_{uT1}$ as a function of T will yield a curve similar to curve 1 in FIG. 3. In this case, $f_{uT1}$ is only slightly greater than $f_{sT1}$ and Case 2 applies. The population curve (b) for this case, in comparison with the control population curve (a), demonstrates this point.

The principles of the present invention will, therefore, consequently permit the discrimination between two populations of cells which may have slightly different fluorescent staining characteristics.

In a concurrently filed copending application of Peter J. Natale, (ORI-27) U.S. Ser. No. 178,481, filed Aug. 15, 1980 now issued as U.S. Pat. No. 4,336,029 and entitled "Method and Reagents for Quantitative Determination of Reticulocytes and Platelets in Whole Blood", assigned to the assignee hereof, there is described a preferred reagent for utilization in accordance with the principles of the present invention. The copending Natale application utilizes the dye known as acridine orange, and employs a formulation which takes advantage of the cationic/anionic reaction between acridine orange and ribo-dioxyribo-nucleic compounds. These reactions result in complexes which fluoresce in the red or green wavelength range, when excited with appropriate radiation. Since both platelets and reticulocytes contain forms of ribonucleic compounds, they will both form populations of cell-dye complexes having fluorescence in the red or green wavelength ranges. These populations of cells may be distinguished from other cells and each other by their respective light scatter and fluorescent emission intensity characteristics in accordance with the principles of the present invention. An altered formulation which prevented cell staining in the presence of acridine orange would allow a control sample from which $f_{uT1}$ could be determined. Alternatively, cells including reticulocytes and platelets could be stained with the dye known as pyromin Y in accordance with the method of H. J Tanke et al (cytometryl; 313°–320° (1981). In this method, cells are washed free of unbound dye, and an unstained sample could serve as proper control to determine $f_{uT1}$. It will be appreciated that the entire foregoing procedure could well be embodied by specifically designed, hardwired apparatus including large numbers of registers, encoders, multiplexers, and the like standard digital processing equipment. In fact, however, it is far preferable to conduct these procedures by means of suitably programmed digital computers. Numerous such apparatus are commercially available and in general use.

Having described the preferred method of discrimination of overlapping subpopulations on a fluorescence distribution histogram, it will be appreciated that software designers of ordinary skill in the art may, depending upon the operating system being employed, and their own desires and facility in terms of utilizing machine language and the commercial operating system, accomplish the requisite tasks expeditiously. So also could digital hardware engineers ply their skills to fabricate hardwired versions. To be noted, however, is that the principles of the present invention are not directed per se to a purely mathematical formula, and are not intended to appropriate such purely mathematical processing. Rather, it is contemplated in accordance with the principles of the present invention that the mathematical manipulations taught may be employed advantageously (so long as they may be accommodated by the memory, speed, and the like parameters of the hardware system being employed) in order to discriminate populations of cells being studied which have overlapping histograms forming a composite fluorescence distribution histogram in order to discriminate the types of cells being studied in accordance with the principles of the present invention.

The significance of the method and approach of the principles of the present invention may be appreciated when reviewing the numerous complicated statistical techniques that have been formulated to aid in extrapolating and curve fitting techniques and the coincident corrections often required. Although the present system may not yield an exact number, it is capable of efficiently obtaining, with a minimum of time for computation required, useful and basic relationships between populations of different types of cells found within a single mixture.

It will be appreciated that the foregoing has set forth preferred and illustrative embodiments of the principles of the present invention, but that numerous alternative embodiments may occur to those of ordinary skill in the art without departure from the spirit or scope of the present invention.

What is claimed is:

1. A method for determining the number of stained cells in a sample having a mixture of stained and unstained cells using a control population of unstained cells comprising the steps of:
   (a) providing the sample and a separate control population of unstained cells having a determinable fluorescence distribution and number of cells;
   (b) passing, separately, at least a portion of said sample and said control population substantially a cell at a time through an area of focused optical stimulation, said area having a cross section of dimension comparable to the expected dimension of the cells;
   (c) detecting fluorescent light stimulated from cells of said sample and said control population in said area;
   (d) selecting a relatively low threshold value of fluorescence intensity;
   (e) identifying, in the control population, the number of control cells below said threshold value and the total number of control cells and relating said control cell numbers for determining a first fraction;
   (f) counting, in the sample, the number of sample cells below said threshold value and the total number of sample cells and relating said sample numbers for determining a second fraction; and
   (g) relating said first fraction to said second fraction for discriminating the number of stained cells in said sample mixture.

2. A method as provided in claim 1 wherein said selecting step comprises:
   a. forming a ratio of said second fraction to said first fraction; and
   b. selecting a threshold value in a region where the ratio as a function of threshold value is approximately constant.

3. A method as provided in claim 2 wherein the relating step comprises approximating the fraction of stained cells in said sample mixture as equal to said ratio substrated from one.

* * * * *

UNITED STATES PATENT AND TRADEMARK OFFICE
CERTIFICATE OF CORRECTION

PATENT NO. : 4,475,236

DATED : October 2, 1984

INVENTOR(S) : Robert A. Hoffman

It is certified that error appears in the above—identified patent and that said Letters Patent is hereby corrected as shown below:

Col. 8, line 67 "substrated" should be --subtracted--.

Signed and Sealed this

Thirty-first Day of December 1985

[SEAL]

Attest:

*Attesting Officer*

DONALD J. QUIGG

*Commissioner of Patents and Trademarks*